[54] 5-DICHLOROACETAMIDO-4-NITRO-1-ARYL-PYRAZOLES, COMPOSITION CONTAINING THEM, AND HERBICIDAL AND PLANT GROWTH REGULATING METHOD OF USING THEM

[75] Inventors: Reinhold Gehring, Wuppertal; Otto Schallner, Monheim; Jörg Stetter, Wuppertal; Albrecht Marhold; Hans-Joachim Santel, both of Leverkusen; Robert R. Schmidt; Klaus Lürssen, both of Bergisch-Gladbach, all of Fed. Rep. of Germany

[73] Assignee: Bayer Aktiengesellschaft, Leverkusen, Fed. Rep. of Germany

[21] Appl. No.: 934,067

[22] Filed: Nov. 24, 1986

[30] Foreign Application Priority Data

Dec. 5, 1985 [DE] Fed. Rep. of Germany ....... 3543033
May 28, 1986 [DE] Fed. Rep. of Germany ....... 3617977

[51] Int. Cl.$^4$ .................... A01N 43/56; C07D 231/40
[52] U.S. Cl. ......................................... 71/92; 548/362
[58] Field of Search ............................ 548/362; 71/92

[56] References Cited

FOREIGN PATENT DOCUMENTS 3402308  8/1985  Fed. Rep. of Germany .......... 71/92

*Primary Examiner*—Mary C. Lee
*Assistant Examiner*—Kurt G. Briscoe
*Attorney, Agent, or Firm*—Sprung Horn Kramer & Woods

[57] ABSTRACT

5-Dichloracetamido-4-nitro-1-aryl-pyrazoles of the formula

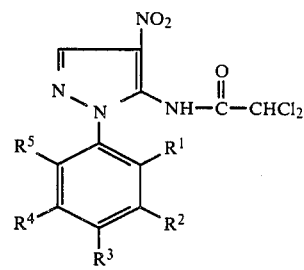

in which
$R^1$ represents hydrogen, fluorine, chlorine or bromine,
$R^2$ represents hydrogen, fluorine or chlorine,
$R^3$ represents halogen, halogenoalkyl, halogenoalkoxy, halogenoalkylthio or halogenoalkylsulphonyl,
$R^4$ represents hydrogen, fluorine, or chlorine, and
$R^5$ represents fluorine, chlorine or bromine, but in the case in which $R^1$ and $R^5$ simultaneously represent chlorine and in addition $R^2$ and $R^4$ simultaneously represent hydrogen, $R^3$ does not represent chlorine or trifluoromethyl, exhibit herbicidal and plant growth-regulating properties. Novel intermediates therefor are also shown.

12 Claims, No Drawings

5-DICHLOROACETAMIDO-4-NITRO-1-ARYL-PYRAZOLES, COMPOSITION CONTAINING THEM, AND HERBICIDAL AND PLANT GROWTH REGULATING METHOD OF USING THEM

The invention relates to new 5-dichloroacetamido-4-nitro-1-aryl-pyrazoles, several processes for their preparation, their use as herbicides and growth regulators and new intermediates for their preparation.

It is already known that certain 5-halogenoacylamino-4-nitro-1-aryl-pyrazoles, such as, for example, 5-(ω-chlorobutyramido)-4-nitro-1-(2,6-dichloro-4-trifluoromethyl-phenyl)-pyrazole, possess herbicidal properties (see U.S. Pat. No. 4,614,533).

However, the herbicidal activity of these previously known compounds with respect to problem weeds is, like their toleration by important crop plants, not always completely satisfactory in all fields of use.

New 5-dichloroacetamido-4-nitro-1-aryl-pyrazoles of the general formula (I)

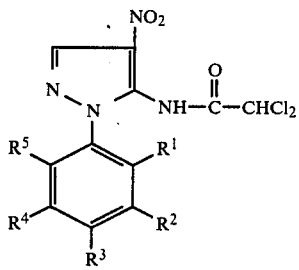

in which
$R^1$ represents hydrogen, fluorine, chlorine or bromine,
$R^2$ represents hydrogen, fluorine or chlorine,
$R^3$ represents halogen, halogenoalkyl, halogenoalkoxy, halogenoalkylthio or halogenoalkylsulphonyl,
$R^4$ represents hydrogen, fluorine or chlorine and
$R^5$ represents fluorine, chlorine or bromine, but in the case in which $R^1$ and $R^5$ simultaneously represent chlorine and in addition $R^2$ and $R^4$ simultaneously represent hydrogen, $R^3$ does not represent chlorine or trifluoromethyl, have been found.

It has furthermore been found that the new 5-dichloroacetamido-4-nitro-1-aryl-pyrazoles of the general formula (I)

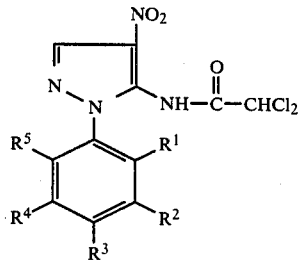

in which
$R^1$ represents hydrogen, fluorine, chlorine or bromine,
$R^2$ represents hydrogen, fluorine, or chlorine,
$R^3$ represents halogen, halogenoalkyl, halogenoalkoxy, halogenoalkylthio or halogenoalkylsulphonyl,
$R^4$ represents hydrogen, fluorine or chlorine and
$R^5$ represents fluorine, chlorine or bromine, but in the case in which $R^1$ and $R^5$ simultaneously represent chlorine and in addition $R^2$ and $R^4$ simultaneously represent hydrogen, $R^3$ does not represent chlorine, or trifluoromethyl,
are obtained if
(a) 5-amino-4-nitro-1-aryl-pyrazoles of the formula (II)

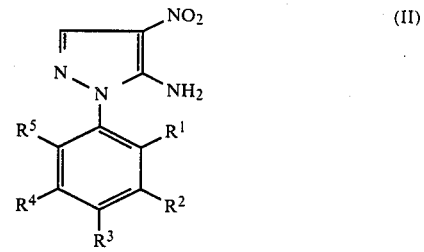

in which $R^1$, $R^2$, $R^3$, $R^4$ and $R^5$ have the meaning given above, are reacted with dichloroacetyl compounds of the formula (III)

in which E represents an electron-attracting leaving group, if appropriate in the presence of a diluent and, if appropriate, in the presence of an acidic or basic catalyst, or, if (b) 5-dichloroacetamido-1-aryl-pyrazoles which are unsubstituted in the 4-position, of the formula (IV)

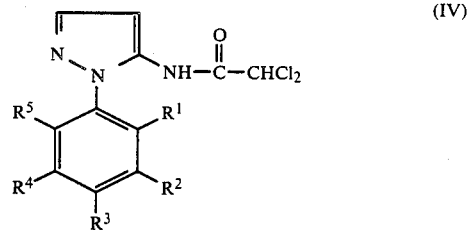

in which $R^1$, $R^2$, $R^3$, $R^4$ and $R^5$ have the meaning given above, are reacted with nitric acid, if appropriate in the presence of a diluent and, if appropriate, in the presence of a catalyst.

Finally, it has been found that the new 5-dichloroacetamido-4-nitro-1-aryl-pyrazoles of the formula (I) have a herbicidal and growth-regulating action.

Surprisingly, the 5-dichloroacetamido-4-nitro-1-aryl-pyrazoles according to the invention, of the general formula (I), while exhibiting comparably good selectivity in useful plants, have a substantially better herbicidal activity with respect to problem weeds than the 5-halogenoacylamino-4-nitro-1-arylpyrazoles known from the prior art, such as, for example, 5-(ω-chlorobutyramido)-4-nitro-1-(2,6-dichloro-4-trifluoromethyl-phenyl)-pyrazole, which are similar compounds chemically and in terms of their action.

Formula (I) gives a general definition of the 5-dichloroacetamido-4-nitro-1-aryl-pyrazoles according to the invention. Preferred compounds of the formula (I) are those
in which
$R_1$ represents hydrogen, fluorine, chlorine or bromine,
$R^2$ represents hydrogen, fluorine or chlorine, $R^3$ represents fluorine, chlorine, bromine or halogenoalkyl, halogenoalkoxy, halogenoalkylthio or halogenoalkylsulphonyl, each of which is straight-chain or branched and each of which has 1 to 4 carbon atoms and 1 to 9 identical or different halogen atoms (in particular fluorine, chlorine or bromine), $R^4$ represents hydrogen, fluorine or chlorine and $R^5$ represents fluorine, chlorine or bromine, but in the case in which $R^1$ and $R^5$ simultaneously represent chlorine and in addition $R^2$ and $R^4$ simultaneously represent hydrogen, $R^3$ does not represent chlorine or trifluoromethyl.

Particularly preferred compounds of the formula (I) are those
in which
$R^1$ represents hydrogen, fluorine, chlorine or bromine,
$R^2$ represents hydrogen, fluorine or chlorine,
$R^3$ represents fluorine, chlorine, bromine, trifluoromethyl, difluoromethyl, fluoromethyl, trichloromethyl, dichlorofluoromethyl, difluorochloromethyl, pentafluoroethyl, trifluoromethoxy, trichloromethoxy, trifluoromethylthio, trifluoromethylsulphonyl, · difluorochloromethylsulphonyl, dichlorofluoromethylsulphonyl or pentafluoroethylsulphonyl,
$R^4$ represents hydrogen, fluorine, or chlorine and
$R^5$ represents fluorine, chlorine or bromine, but in the case in which $R^1$ and $R^5$ simultaneously represent chlorine and in addition $R^2$ and $R^4$ simultaneously represent hydrogen, $R^3$ does not represent chlorine or trifluoromethyl.

Reference may be made to the individual compounds of the formula (I) mentioned in the preparation examples.

If, for example, 5-amino-4-nitro-1-(2,3,6-trichloro-4-trifluoromethyl-phenyl)-pyrazole and dichloroacetic anhydride are used as starting materials, the course of the reaction of process (a) according to the invention can be represented by the following equation:

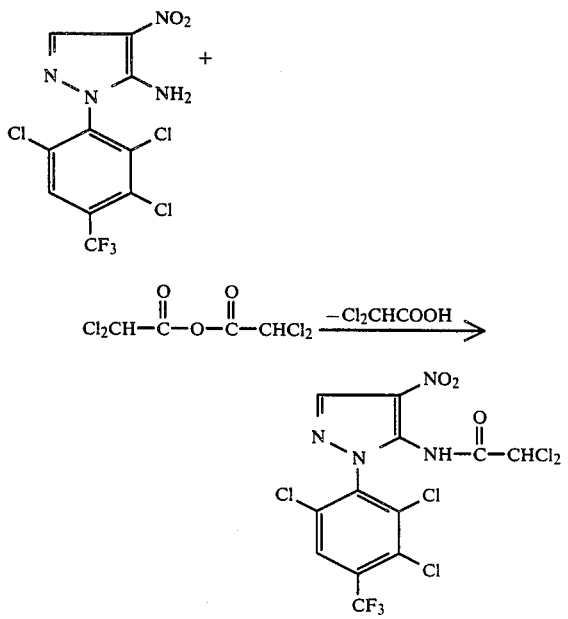

If, for example, 5-dichloroacetamido-1-(2,6-dichloro-4-trifluoromethylsulphonyl-phenyl)-pryazole is used as a starting compound, the course of the reaction of process (b) according to the invention can be represented by the following equation:

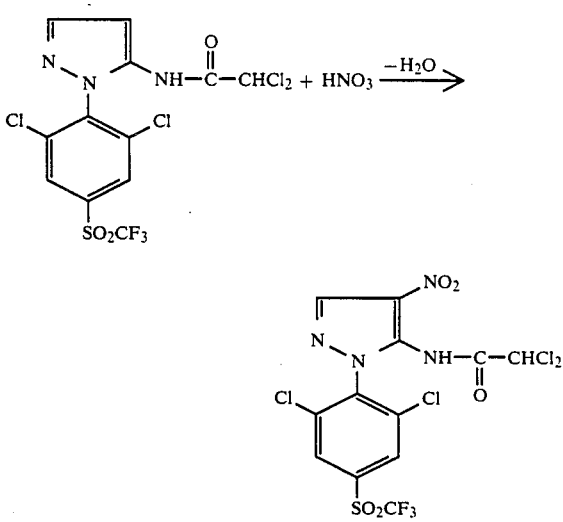

Formula (II) gives a general definition of the 5-amino-4-nitro-pyrazoles required as starting materials for carrying out process (a) according to the invention. In this formula (II), $R^1$, $R^2$, $R^3$, $R^4$ and $R^5$ preferably represent those radicals which have already been mentioned in connection with the description of the substances according to the invention, of the formula (I), as being preferred for these substituents.

Some of the 5-amino-4-nitro-pyrazoles of the formula (II) are known (see DE-OS (German Published Specification) No. 3,402,308) and can be prepared by the processes described there.

Unknown to date are the 5-amino-4-nitro-pyrazoles of the formula (IIa)

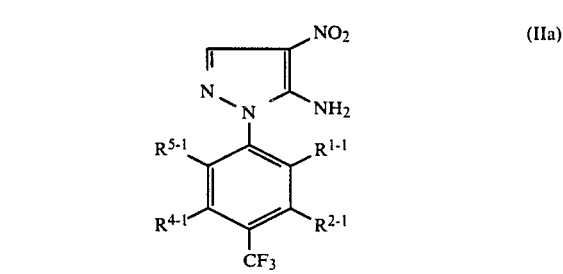

in which
$R^{1-1}$, $R^{2-1}$ and $R^{4-1}$ independently of one another each represent hydrogen, fluorine or chlorine and
$R^{5-1}$ represent fluorine or chlorine, with the exception of the combinations in which $R^{1-1}$, $R^{2-1}$, $R^{4-1}$ and $R^{5-1}$ simultaneously represent fluorine, $R^{1-1}$, $R^{2-1}$, $R^{4-1}$ and $R^{5-1}$ simultaneously represent chlorine, $R^{1-1}$ and $R^{5-1}$ represent chlorine and $R^{2-1}$ and $R^{4-1}$ simultaneously represent either hydrogen or fluorine, and $R^{1-1}$, $R^{2-1}$ and $R^{4-1}$ represent hydrogen and $R^{5-1}$ simultaneously represents chlorine and $R^{1-1}$, $R^{2-1}$ and $R^{5-1}$ represent chlorine and $R^{4-1}$ simultaneously represents hydrogen.

Preferred compounds of the formula (IIa) are those in which $R^{1-1}$, $R^{2-1}$, $R^{4-1}$ and $R^{5-1}$ have the preferred meanings stated in the description of the phenylhydrazines of the formula (V).

The compounds of the formula (IIa) can be prepared by a process in which arylhydrazines of the formula (V)

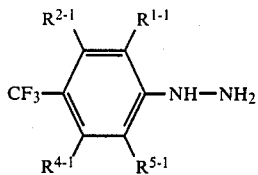  (V)

in which $R^{1-1}$, $R^{2-1}$, $R^{4-1}$ and $R^{5-1}$ have the meaning given above, are reacted with 2-halogenoacrylonitriles of the formula (VI)

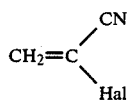  (VI)

in which Hal represents halogen, in particular chlorine or bromine, either initially in a first stage, if appropriate in the presence of a diluent, such as, for example, glacial acetic acid or ethanol, and, if appropriate, in the presence of a reaction auxiliary, such as, for example, sodium acetate, at temperatures between −20° C. and +20° C. to give the arylhydrazine derivatives of the formula (VII)

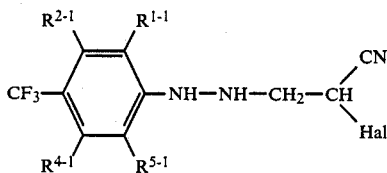  (VII)

in which $R^{1-1}$, $R^{2-1}$, $R^{4-1}$, $R^{5-1}$ and Hal have the meaning given above, and this is cyclized in a second stage, if appropriate in the presence of a diluent, such as, for example, ethylene glycol monoethyl ether and, if appropriate, in the presence of an acidic catalyst, such as, for example, sulphuric acid or phosphoric acid, at temperatures between +50° C. and +150° C., or cyclization is carried out directly in one reaction step, without isolation of the intermediate of the formula (VII), if appropriate in the presence of a diluent, such as, for example, ethylene glycol monoethyl ether or ethanol, at temperatures between +50° C. and +150° C., and the 5-aminopyrazoles of the formula (VIII)

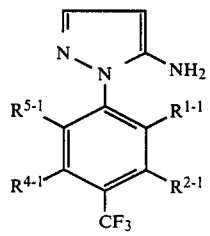  (VIII)

in which $R^{1-1}$, $R^{2-1}$, $R^{4-1}$ and $R^{5-1}$ have the meaning given above which are unsubstituted in the 4-position and are obtainable in this manner are nitrated in a subsequent reaction with a nitrating agent, such as, for example, nitric acid, if appropriate in the presence of a diluent, such as, for example, glacial acetic acid, and, if appropriate, in the presence of a reaction auxiliary, such as, for example, acetic anhydride, at temperatures between −20° C. and +50° C.

It may be advantageous to protect the amino group in the 5-position of the pyrazole ring, prior to the nitration reaction, with the aid of the customary protective group technique, for example by acylation, and to eliminate the amino protective group when nitration is complete, likewise in a customary manner, for example by hydrolysis with aqueous or alcoholic base.

In appropriate concentrations, the new 5-amino-4-nitropyrazoles of the formula (II-a) also exhibit very good herbicidal activity, in particular selective herbicidal activity.

The arylhydrazines of the formula (V)

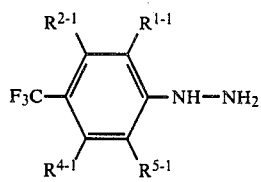  (V)

in which
$R^{1-1}$, $R^{2-1}$ and $R^{4-1}$ independently of one another each represent hydrogen, fluorine or chlorine and
$R^{5-1}$ represents fluorine or chlorine, with the exception of the combinations in which
$R^{1-1}$, $R^{2-1}$, $R^{4-1}$ and $R^{5-1}$ simultaneously represent fluorine, $R^{1-1}$, $R^{2-1}$, $R^{4-1}$ and $R^{5-1}$ simultaneously represent chlorine, $R^{1-1}$ and $R^{5-1}$ represent chlorine and $R^{2-1}$ and $R^{4-1}$ simultaneously represent either hydrogen or fluorine, and $R^{1-1}$,
$R^{2-1}$ and $R^{4-1}$ represent hydrogen and $R^{5-1}$ simultaneously represents chlorine and $R^{1-1}$, $R^{2-1}$, and $R^{5-1}$ represent chlorine and $R^{4-1}$ simultaneously represents hydrogen,
are new and form the subject of the present invention.

The following compounds of the formula (V) are preferred:

| $R^{1-1}$ | $R^{2-1}$ | $R^{4-1}$ | $R^{5-1}$ |
|---|---|---|---|
| Cl | H | F | Cl |
| H | H | Cl | Cl |
| H | F | H | Cl |
| Cl | F | F | F |
| Cl | F | H | F |
| Cl | H | H | F |
| F | F | H | F |
| H | F | F | F |
| Cl | H | F | F |

For example, the new arylhydrazines of the formula (V) are obtained if halogenoaromatics of the formula (IX)

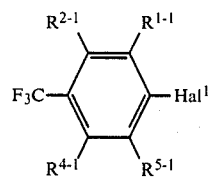  (IX)

in which $R^{1-1}$, $R^{2-1}$, $R^{4-1}$ and $R^{5-1}$ have the meaning given above and Hal$^1$ represents halogen, in particular fluorine or chlorine, are reacted with hydrazine or hydrazinehydrate, if appropriate in the presence of a diluent.

The 2-halogenoacrylonitriles of the formula (VI) and the halogenoaromatics of the formula (IX) are generally known compounds of organic chemistry (see, for example, EP-A-34 402 and U.S. Pat. No. 4,388,472).

The reaction, according to the invention, for the preparation of the arylhydrazines of the formula (V) is carried out in general in the presence of a solvent. Examples of suitable solvents are alcohols, ethers, etheralcohols, tertiary amines and sulphones. Ethanol, dioxane, glycol monomethyl ether, triethylamine, pyridine, picoline and tetramethylenesulphone are particularly suitable.

Suitable temperatures for this reaction are for example, those in the range from 0° to 120° C., temperatures in the range from 50° to 120° C. preferably being used particularly when less reactive compounds of the formula (IX) are employed. In general, it is not necessary to use pressure, unless it is desired to carry out the reaction in a solvent which has a boiling point which is below the desired reaction temperature under atmospheric pressure.

In general, it is advantageous if only small excess amounts of hydrazine are present during the reaction. Preferably, therefore, the compound of the formula (IX) is initially introduced, if appropriate together with a solvent, and hydrazine is then added. Furthermore, it is generally advantageous to avoid the use of relatively large excess amounts of hydrazine, for example more than 1.2 mols of hydrazine per mol of the compound of the formula (IX).

If a compound of the formula (IX) in which Hal$^1$=chlorine is employed, it is very advantageous to add a base, unless a base, for example pyridine, is already being used as the solvent. Examples of suitable bases are tertiary amines, such as triethylamine, pyridine and picoline, and carbonates, bicarbonates and acetates of alkali metals, such as potassium acetate, sodium acetate, potassium carbonate, sodium bicarbonate, sodium carbonate, calcium hydroxide and calcium. Hydrazine can, if appropriate, also serve as this base.

The hydrazine can be employed, for example, in the form of hydrazine hydrate, as well as in anhydrous form or as hydrazine containing up to 80% by weight of water.

In general, the reaction is complete after 1 to 15 hours. The reaction mixture can then be worked up, for example, by a method in which, if appropriate, at least half, preferably at least 80% by weight, of the solvent present is distilled off (the solvent can be reused) and the reaction mixture is then stirred into cold water, and the product of the formula (V) obtained in crystalline form is separated off, if necessary rinsed with a small amount of water and dried. If desired, the product may furthermore be recrystallized, for example from cyclohexane or toluene.

The compounds of the formula (V) are crystalline at room temperature and can be obtained in good yields and in good purities in the manner described. Relatively small amounts of isomers, which are formed, for example, by the introduction of the NH$_2$NH-group at a position other than the para-position with respect to the CF$_3$ group, are substantially removed by the working up procedure described.

Formula (III) gives a general definition of the dichloroacetyl compounds furthermore required as starting materials for carrying out process (a) according to the invention. In this formula (III), E preferably represents halogen, in particular chlorine or bromine, or a dichloroacetyloxy radical.

The dichloroacetyl compounds of the formula (III) are generally known compounds of organic chemistry.

Formula (IV) gives a general definition of the 5-dichloroacetamido-1-aryl-pyrazoles which are unsubstituted in the 4-position and required as starting materials for carrying out process (b) according to the invention. In this formula (IV), $R^1$, $R^2$, $R^3$, $R^4$ and $R^5$ preferably represent those radicals which have already been mentioned in connection with the description of the substances according to the invention, of the formula (I), as being preferred for these substituents.

The dichloroacetamido-1-aryl-pyrazoles of the formula (IV) which are unsubstituted in the 4-position were unknown to date. However, they are obtained analogously to known processes (see, for example, U.S. Pat. No. 4,614,533), if 5-amino-pyrazoles which are unsubstituted in the 4-position, of the formula (X)

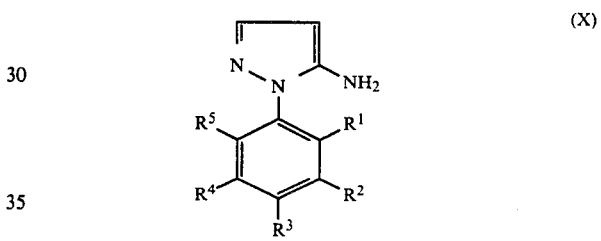

in which $R^1$, $R^2$, $R^3$, $R^4$ and $R^5$ have the meaning given above, are acylated with dichloroacetyl compounds of the formula (III)

in which E has the meaning given above, if appropriate in the presence of a diluent, such as, for example, dichloromethane, and, if appropriate, in the presence of an acid-binding agent, such as, for example, pyridine, analogously to the procedure for process (a) according to the invention, at temperatures between −20° C. and +120° C.

Some of the 5-amino-pyrazoles of the formula (X) which are unsubstituted in the 4-position are known (see, for example, U.S. Pat. No. 4,614,533) and some are new (see compounds of the general formula (VIII)) and can be prepared analogously to the known processes.

Suitable diluents for carrying out process (a) according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran and ethylene glycol dimethyl and diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, sulphoxides, such as dimethyl sulphoxide, and carboxylic acids, such as acetic acid.

Process (a) according to the invention is carried out, if appropriate, in the presence of a suitable acidic or basic catalyst.

Suitable catalysts are all customary inorganic or organic bases or anhydrous protic acids. These include, for example, alkali metal hydroxides, such as sodium hydroxide or potassium hydroxide, alkali metal carbonates, such as sodium carbonate, potassium carbonate or sodium bicarbonate, tertiary amines, such as triethylamine, N,N-dimethylaniline, pyridine, N,N-dimethylaminopyridine, diazabicyclooctane (DABCO), diazabicyclononene (DBN) or diazabicycloundecene (DBU), and anhydrous sulphuric acid, phosphoric acid and hydrochloric acid.

In carrying out process (a) according to the invention, the reaction temperatures can be varied within a relatively wide range. In general, the process is carried out at temperatures between $-20°$ C. and $+150°$ C., preferably at temperatures between $0°$ C. and $120°$ C.

To carry out process (a) according to the invention, 1.0 to 5.0 mols, preferably 1.0 to 2.0 mols, of the dichloroacetyl compound of the formula (III) and, if appropriate, 1.0 to 5.0 mols, preferably 1.0 to 2.0 mols of an acid-binding agent are generally employed per mol of 5-amino-4-nitro-1-aryl-pyrazole of the formula (II). The reaction procedure, working-up and isolation of the reaction products of the formula (I) are carried out by customary, generally known methods.

Suitable diluents for carrying out process (b) according to the invention are all solvents which can customarily be used for nitration reactions of this type. The acids which are suitable as reagents, or their mixtures with a catalyst acid, such as, for example, sulphuric acid, nitric acid, acetic anhydride or nitrating acid, are preferably used simultaneously as the diluent. Inert organic solvents, such as, for example, glacial acetic acid or chlorinated hydrocarbons, such as methylene chloride, chloroform or carbon tetrachloride, may also be suitable as diluents.

Other suitable catalysts or reaction auxiliaries for carrying out process (b) according to the invention are the catalysts customarily used for nitrations of this type; acidic catalysts, such as, for example, sulphuric acid or acetic anhydride, are preferably used.

For carrying out process (b) according to the invention, the reaction temperatures can be varied within a relatively wide range. In general, the process is carried out at temperatures between $-50°$ C. and $+120°$ C., preferably at temperatures between $-20°$ C. and $+150°$ C.

To carry out process (b) according to the invention 1.0 to 100.0 mols, preferably 1.0 to 50.0 mols, of nitric acid and, if appropriate, 0.1 to 10 mols of catalyst are generally employed per mol of 5-dichloroacetamido-1-aryl-pyrazole unsubstituted in the 4-position, of the formula (IV). The reaction procedure, working-up and isolation of the reaction products of the formula (I) are carried out by customary, generally known methods.

The active compounds according to the invention can be used as defoliants, desiccants, agents for destroying broad-leaved plants and, especially, as week-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phelum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative trees plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used with particularly good success for selectively combating monocotyledon and dicotyledon weeds, in particular in monocotyledon cultures, such as barley or wheat.

The precursors of the formula (IV), too, have good herbicidal activity when used in appropriate amounts.

The active compounds according to the invention engage in the metabolism of the plants and can therefore be employed as growth regulators. p Experience to date of the mode of action of plant growth regulators has shown that an active compound can also exert several different actions on plants. The actions of the compounds depend essentially on the point in time at which they are used, relative to the state of development of the plant, and on the amounts of active compound applied to the plants or their environment and they way in which the compounds are applied. In every case, growth regulators are intended to influence the crop plants in the particular manner desired.

The amount of leaves on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted to the customary formulations, such as solutions, emulsions, wettable powders, suspensions, powders, dusting agents, pastes, soluble powders, granules, suspension emulsion concentrates, foams, natural and synthetic materials impregnated with active compound, very fine capsules in polymeric substances and in coating compositions for seed, and ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkyl-naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carries are meant liquids which are gaseous at normal temperature and under normal pressure, for example aerosol propellants, such as halogenated hydrocarbons as well as butane, propane, nitrogen and carbon dioxide.

As solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

When used as herbicides, the active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugar beets, and 4-amino-6-(1,1-dimethylethyl)-3-methylthio-1,2,4-triazin-5(4H)-one for combating weeds in soy beans.

Mixtures with N,N-dimethyl-N'-(3-chloro-4-methylphenyl)-urea; N,N-dimethyl-N'-(4-isopropylphenyl)-urea; 4-amino-6-t-butyl-3-ethylthio-1,2,4-triazin-5(4H)-one; 2,4-dichlorophenoxyacetic acid; 2,4-dichlorophenoxypropionic acid; (2-methyl-4-chlorophenoxy)-acetic acid; (4-chloro-2-methylphenoxy)-propionic acid; 2-benzyloxyethyl, trimethylsilylmethyl or 2,2-diethoxyethyl 2-[4-(3,5-dichloropyrid-2-yloxy)-phenoxy]-propionate; methyl 5-(2,4-dichlorophenoxy)-2-nitrobenzoate; 3,5-diiodo-4-hydroxybenzonitrile; 3-isopropyl-2,1,3-benzothiadiazin-4-one 2,2-dioxide; 2-chloro-N-{[(4-methoxy-6-methyl-1,3,5-triazin-2-yl)-amino]-carbonyl}-benzenesulphonamide; 4-ethylamino-2-t-butylamino-6-methylthio-s-triazine; N-methyl-2-(1,3-benzothiazol-2-yloxy)-acetanilide; N,N-diisopropyl-S-(2,3,3-trichloroallyl)-thiolcarbamate; N-(1-ethylpropyl)-3,4-dimethyl-2,6-dinitroaniline; 3,5-dibromo-4-hydroxybenzonitrile and methyl 2-[4-(2,4-dichlorophenoxy)-phenoxy]-propionate may be advantageous.

Some mixtures surprisingly also exhibit a synergistic effect.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface preferably between 0.05 and 5.0 kg per ha.

When used as growth regulators, the active compounds according to the invention can be present in the formulations likewise as a mixture with other known active compounds, such as fungicides, insecticides, acaricides and herbicides, and also as mixtures with fertilizers and other growth regulators.

The active compound can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, brushing on and the like. It is furthermore possible to apply the active compounds by the ultra-low volume method, or to inject the active compound preparation or the active compound itself into the soil. The seed of the plants can also be treated.

The amounts used can be varied within a substantial range. In general, 0.01 to 50 kg, preferably 0.05 to 10 kg, of the active compound are employed per hectare of soil surface.

As regards the time of application, the rule is that the growth regulators are applied within a preferred period of time, the exact definition of which depends on the climatic and vegetative circumstances.

The preparation and the use of the active compounds according to the invention are evident from the examples which follow.

PREPARATION EXAMPLES

Example 1

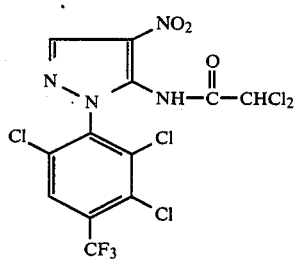

Process (b)

1.2 ml (0.0129 mol) of acetic anhydride and 0.6 ml (0.0143 mol) of 98% strength nitric acid are added in succession to 5 g (0.0113 mol) of 5-dichloroacetamido-1-(2,3,6-trichloro-4-trifluoromethyl-phenyl)-pyrazole in 10 ml of glacial acetic acid at room temperature. The mixture is stirred for 20 hours, after which it is evaporated down in vacuo, the residue is taken up in 50 ml of dichloromethane and the solution is washed in succession with saturated sodium bicarbonate solution and saturated sodium chloride solution. The organic phase is dried over magnesium sulphate and freed from the solvent in vacuo. 4.2 g (76.4% of theory) of 5-dichloroacetamido-4-nitro-1-(2,3,6-trichloro-4-trifluoromethyl-phenyl)-pyrazole of melting point 112° C.-120° C. are obtained.

Example 2

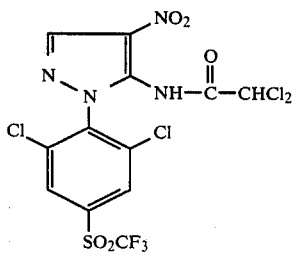

Process (b)

1.2 ml (0.0129 mol) of acetic anhydride and 0.6 ml (0.0143 mol) of 98% strength nitric acid are added in succession to 5.2 g (0.0110 mol) of 5-dichloroacetamido-1-(2,6-dichloro-4-trifluoromethylsulphonyl)-pyrazole in 10 ml of glacial acetic acid at room temperature. The mixture is stirred for 20 hours, after which it is evaporated down in vacuo, the residue is taken up in 50 ml of dichloromethane and the solution is washed in succession with saturated sodium bicarbonate solution and saturated sodium chloride solution. The organic phase is dried over magnesium sulphate and freed from the solvent in vacuo. 4.7 g (83.9% of theory) of 5-dichloroacetamido-4-nitro-1-(2,6-dichloro-4-trifluoromethylsulphonyl-phenyl)-pyrazole of melting point 138° C.-142° C. are obtained.

Example 3

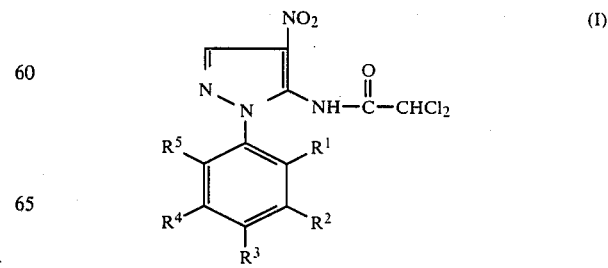

Process (a)

3.0 ml (0.031 mol) of dichloroacetyl chloride and 2 drops of 96% strength sulphuric acid are added to 3.0 g (0.0084 mol) of 5-amino-1-(2,6-dichloro-3-fluoro-4-trifluoromethylphenyl)-4-nitropyrazole in 10 ml of dichloroacetic acid at room temperature. The mixture is stirred for 4 hours at 140° C., after which it is discharged onto 50 ml of water and 50 ml of dichloromethane. The organic phase is separated off, washed in succession with saturated sodium bicarbonate solution and saturated sodium chloride solution, dried over magnesium sulphate and freed from the solvent in vacuo. 3.2 g (81.5% of theory) of 5-dichloroacetamido-(2,6-dichloro-3-fluoro-4-trifluoromethylphenyl)-4-nitropyrazole of melting point 115°-117° C. are obtained.

The following 5-dichloroacetamido-4-nitro-1-aryl-pyrazoles of the general formula (I) are obtained in a corresponding manner and in accordance with the general data for preparation:

TABLE 1

Structure: benzene ring with substituents R¹, R², R³, R⁴, R⁵

| Example No. | Substituents | Melting point/°C. |
|---|---|---|
| 4 | R¹=Cl, R⁴=CF₃ | 134–138 |
| 5 | R¹=Cl, R⁴=OCF₃ | 82–85 |
| 6 | R¹=Cl, R⁵=Cl, R³=SCF₃ | 118–119 |
| 7 | R¹=Cl, R²=Cl, R⁵=Cl, R³=OCF₃ | 88 |
| 8 | R¹=Cl, R²=Cl, R⁵=Cl, R³=SCF₃ | 106 |
| 9 | R¹=Br, R⁵=Cl, R³=CF₃ | 136 |
| 10 | R¹=Cl, R²=F, R⁵=Cl, R⁴=F, R³=Cl | 160–164 |
| 11 | R¹=Cl, R²=F, R⁵=Cl, R⁴=F, R³=CF₃ | 120–121 |
| 12 | R¹=Cl, R⁵=Cl, R³=SO₂CF₂Cl | 134 |
| 13 | R¹=Br, R³=CF₃ | 143 |
| 14 | R¹=Br, R⁵=Br, R³=CF₃ | — |
| 15 | R³=CF₃, R⁴=F, R⁵=Cl | 141–148 |
| 16 | R¹=F, R³=CF₃, R⁵=Cl | 101–104 |
| 17 | R¹=Cl, R³=CF₃, R⁴=F, R⁵=F | — |
| 18 | R³=CF₃, R⁴=Cl, R⁵=Cl | — |
| 19 | R¹=Cl, R²=F, R³=CF₃, R⁴=F, R⁵=F | — |

TABLE 1-continued

| Example No. | $R^1$ $R^2$ $R^3$ $R^4$ $R^5$ | Melting point/°C |
|---|---|---|
| 20 | 1,4-dibromobenzene (Br, Br) | 55–65 |

PREPARATION OF THE STARTING MATERIALS OF THE FORMULA (IIa)

Example IIa-1

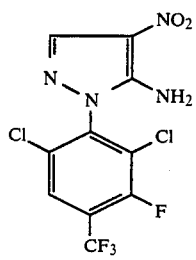

10 g (0.032 mol) of 5-amino-1-(2,6-dichloro-3-fluoro-4-trifluoromethylphenyl)-pyrazole are introduced in portions into a boiling solution of 2.3 ml (0.034 mol) of 67% strength nitric acid and 0.1 g of urea in 30 ml of water. The suspension is allowed to cool, and the precipitate is filtered off and dried in vacuo at room temperature. The dry precipitate is introduced into 40 ml of 98% strength sulphuric acid at −5° C., and the mixture is stirred for 12 hours at 0°–5° C. Thereafter, the reaction mixture is introduced into 350 ml of water, boiled up for a short time and allowed to cool to room temperature and the precipitate is filtered off. The precipitate is washed neutral with water and dried in vacuo at 40°–50° C. 7.0 g (61% of theory) of 5-amino-1-(2,6-dichloro-3-fluoro-4-trifluoromethylphenyl)-4-nitropyrazole of melting point 156° C. are obtained.

The following 5-amino-1-aryl-4-nitropyrazoles of the general formula (IIa) are obtained in a corresponding manner and in accordance with the general data for preparation:

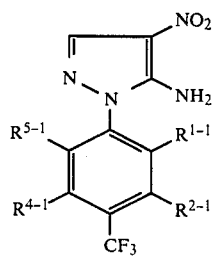

(IIa)

TABLE 2

| Example No. | $R^{1-1}$ $R^{2-1}$ $R^{4-1}$ $R^{5-1}$ (CF3) | Melting point/0° C. |
|---|---|---|
| IIa-2 | 3-Cl, 2-F, CF3 | 125–128 |
| IIa-3 | 2-Cl, 5-F, CF3 | 171 |
| IIa-4 | 2-Cl, 3-F, 5-F, 6-F, CF3 | 112 |
| IIa-5 | 2-Cl, 3-Cl, CF3 | — |
| IIa-6 | 2-Cl, 5-F, 6-F, CF3 | — |
| IIa-7 | 2-F, 5-F, CF3 | 96–99 |

PREPARATION OF THE STARTING MATERIALS OF THE FORMULA (IV)

Example IV-1

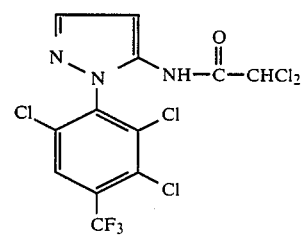

15.3 g (0.145 mol) of anhydrous sodium carbonate and 4.76 ml (0.048 mol) of 98% strength dichloroacetyl chloride are added in succession, at 5° C. to 10° C., to 8.0 g (0.024 mol) of 5-amino-1-(2,3,6-trichloro-4-trifluoromethyl-phenyl)-pyrazole in 80 ml of dichloromethane. The mixture is stirred for 4 hours at 5° C.–10° C. and for 13 hours at room temperature. The mixture is diluted with 80 ml of dichloromethane, filtered, and washed in succession with water and saturated sodium chloride solution. The organic phase is dried over magnesium sulphate and freed from the solvent in vacuo. 10.0 g (93.5% of theory) of 5-dichloroacetamido-1-(2,3,6-trichloro-4-trifluoromethyl-phenyl)-pyrazole of melting point 156° C.–161° C. are obtained.

The following 5-dichloroacetamido-1-aryl-pyrazoles of the general formula (IV) which are unsubstituted in the 4-position are obtained in a corresponding manner and in accordance with the general data for preparation:

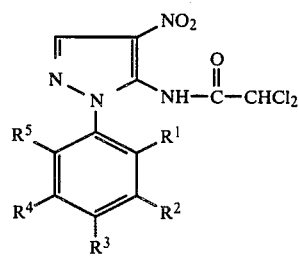

(IV)

TABLE 3

| Example No. | $R^1$ | $R^2$ | $R^3$ | $R^4$ | $R^5$ | Melting point/0° C. |
|---|---|---|---|---|---|---|
| IV-2 | | Cl | SO$_2$CF$_3$ | Cl | | 69–73 |
| IV-3 | | Cl | OCF$_3$ | | | 94–97 |
| IV-4 | | Cl | SCF$_3$ | Cl | | 150–151 |
| IV-5 | Cl | Cl | OCF$_3$ | Cl | | 138 |
| IV-6 | Cl | Cl | SCF$_3$ | | Cl | 146 |
| IV-7 | Cl | F | Cl | F | Cl | 128–129 |
| IV-8 | Cl | F | CF$_3$ | F | Cl | 146–149 |
| IV-9 | | Cl | SO$_2$CF$_2$Cl | Cl | | 146–148 |
| IV-10 | | Cl | CF$_3$ | | | 112–114 |
| IV-11 | | Br | CF$_3$ | Cl | | 156 |
| IV-12 | | Br | CF$_3$ | | | |
| IV-13 | | Br | CF$_3$ | Br | | |

TABLE 3-continued

R¹-R²-R³-R⁴-R⁵ benzene structure

| Example No. | Structure (R¹, R², R³, R⁴, R⁵) | Melting point/0° C. |
|---|---|---|
| IV-14 | CF₃, F, Cl (on ring) | 131–134 |
| IV-15 | Cl, Cl, CF₃, F | 162–165 |
| IV-16 | Cl, CF₃, F | 118–121 |
| IV-17 | Cl, CF₃, F, F | — |
| IV-18 | CF₃, Cl, Cl | — |
| IV-19 | Cl, F, CF₃, F, F | 112–116 |

PREPARATION OF THE STARTING MATERIALS OF THE FORMULA (V)

Example V-1

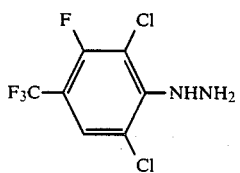

470 g of 3,5-dichloro-2,4-difluorobenzotrifluoride in 1000 ml of ethanol are initially introduced, and 142 g of hydrazine hydrate are metered in, and the mixture is then heated under reflux for 3 hours. Thereafter, the solvent is distilled off under reduced pressure and the residue is stirred into 1 l of cold water. After 30 minutes, the mixture is filtered under suction and the solid product is dried in a through-circulation oven. 445 g of 2,6-dichloro-3-fluoro-4-trifluoromethyl-phenylhydrazine having a melting point of 50° to 51° C. are obtained.

Example V-2

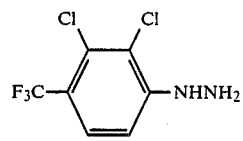

100 g of 2,3,4-trichlorobenzotrifluoride are initially introduced, 200 ml of pyridine are added, followed by 100 g of hydrazine hydrate and the mixture is then heated to the reflux temperture for 12 hours. Thereafter, 90% of the pyridine is distilled off and the remaining residue is stirred into 250 ml of water. The crystalline product is filtered off under suction, washed with a little water and dried. 78 g of 2,3-dichloro-4-trifluoromethyl-phenylhydrazine having a melting point of 79° to 80° C. are obtained.

The compounds of the formula (V) which are listed in the table below are obtained in a corresponding manner, in particular analogously to Example V-1, and in accordance with the general data for preparation:

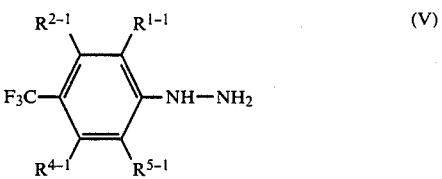

TABLE 4

| Example No. | Structure | Melting point/0° C. |
|---|---|---|
| V-3 | F₃C-, F, F, F, Cl – NHNH₂ | 93–94 |
| V-4 | F₃C-, F, F, Cl – NHNH₂ | 72–73 |
| V-5 | F₃C-, F, Cl – NHNH₂ | 60–61 |
| V-6 | F₃C-, F, Cl – NHNH₂ | 102–103 |

TABLE 4-continued

| Example No. | Structure | Melting point/ 0° C. |
|---|---|---|
| V-7 | 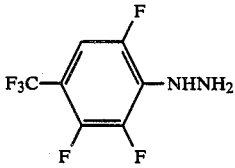 F₃C—⟨F,F,F⟩—NHNH₂ | 60–62 |
| V-8 | 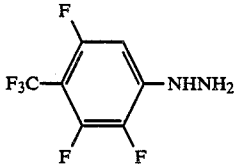 F₃C—⟨F,F,F⟩—NHNH₂ | 69–70 |
| V-9 | 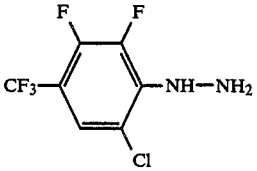 CF₃—⟨F,F,Cl⟩—NH—NH₂ | |

PREPARATION OF THE STARTING MATERIALS OF THE FORMULA (VIII)

Example VIII-1

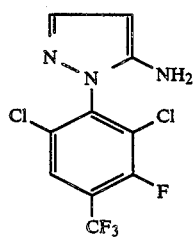

42.6 g (0.162 mol) of 2,6-dichloro-3-fluoro-4-trifluoromethylphenylhydrazine are dissolved in 250 ml of analytical grade methanol, 35 mg of Titriplex III are added and the mixture is heated under reflux. At this temperature, 40 ml (=44 g/0.049 mol) of 98% strength 2-chloroacrylonitrile are added dropwise in the course of 30 minutes. The mixture is stirred for 5 hours at reflux temperature. The reaction mixture is evaporated to dryness. The residue is suspended in 100 ml of trifluoroacetic acid and slowly heated. Stirring is continued for 8 hours at 80°–83° C. The trifluoroacetic acid is distilled off under a slight vacuum, the residue is dissolved in 250 ml of methanol, and 55 g (0.52 mol) of anhydrous sodium carbonate are added. The mixture is stirred for 2 hours, the solvent is stripped off in vacuo and the residue is suspended in 1 liter of water. The precipitate is filtered off under suction, washed neutral with water and dried in vacuo at 50° C.

41.2 g (81% of theory) of 5-amino-1-(2,6-dichloro-3-fluoro-A-trifluoromethylphenyl)-pyrazole of melting point 70°–78° C. are obtained.

The following 5-amino-1-arylpyrazoles of the general formula (VIII) are obtained in a corresponding manner and in accordance with the general data for preparation:

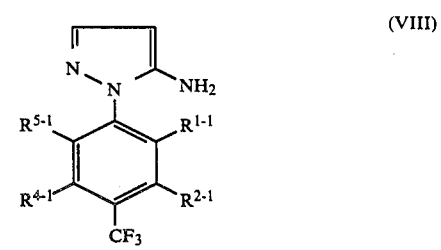
(VIII)

TABLE 5

| | R¹⁻¹ R²⁻¹ CF₃ R⁵⁻¹ R⁴⁻¹ | | |
|---|---|---|---|
| Example No. | R⁵⁻¹ | R⁴⁻¹ | Melting point/0° C. |
| VIII-2 | 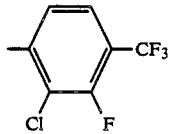 —⟨CF₃, Cl, F⟩ | | 112–114 |
| VIII-3 | Cl | 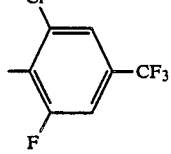 —⟨CF₃, F⟩ | 81–82 |
| VIII-4 | Cl | F 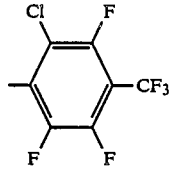 —⟨CF₃, F, F⟩ | oil NMR (CDCl₃) δ = 5.69 ppm (d, 1H), 7.55 ppm (d, 1H) |
| VIII-5 | 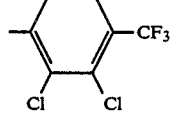 —⟨CF₃, Cl, Cl⟩ | | 139–140 |
| VIII-6 | 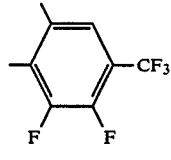 —⟨Cl, CF₃, F, F⟩ | | |
| VIII-7 | 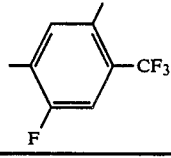 —⟨F, CF₃, F⟩ | | 95–97 |

USE EXAMPLES

The compound given below was employed as a comparative substance in the use examples which follow:

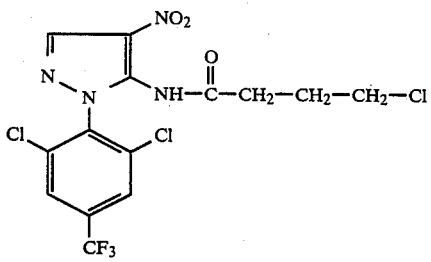

5-(ω-Chlorobutyramido)-4-nitro-1-(2,6-dichloro-4-trifluoromethyl-phenyl)-pyrazole (disclosed in U.S. Pat. No. 4,614,533).

Example A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior activity compared with comparative substance (A) in weeds such as Amaranthus, Galium, Sinapis, Stellaria and Setaria is shown, for example, by the compounds according to preparation Examples 1, 2, 3 and 15.

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, a clearly superior activity against weeds, such as Amaranthus, Galium, Matricaria, Sinapis and Panicum, compared with the comparative substance (A), coupled with comparable crop plant selectivity in, for example, wheat, is shown, for example, by the compounds according to preparation Examples 2 and 15.

Example C

Defoliation and desiccation of the leaves of cotton

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control.

In this test, for example, the compounds according to preparation Examples 1, 3, 4, 9 and 15 are clearly effective defoliants and desiccants.

It will be understood that the specification and examples are illustrative but not limitative of the present invention and that other embodiments within the spirit and scope of the invention will suggest themselves to those skilled in the art.

We claim:

1. A 5-dichloroacetamido-4-nitro-1-aryl-pyrazole of the formula

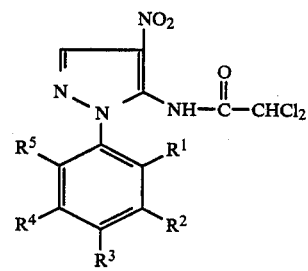

in which
$R^1$ represents hydrogen, fluorine, chlorine or bromine,
$R^2$ represents hydrogen, fluorine or chlorine,
$R^3$ represents fluorine, chlorine, bromine or halogenoalkyl, halogenoalkoxy, halogenoalkylthio or halogenoalkylsulphonyl, each of which is straight-chain or branched and each of which has 1 to 4 carbon atoms and 1 to 9 identical or different halogen atoms,
$R^4$ represents hydrogen, fluorine, or chlorine, and
$R^5$ represents fluorine, chlorine, or bromine, but in the case in which $R^1$ and $R^5$ simultaneously represent chlorine and in addition $R^2$ and $R^4$ simultaneously represent hydrogen, $R^3$ does not represent chlorine or trifluoromethyl.

2. A compound according to claim 1, wherein such compound is 5-dichloroacetamido-4-nitro-1-(2,3,6-trichloro-4-trifluoromethyl-phenyl)-pyrazole of the formula

3. A compound according to claim 1, wherein such compound is 5-dichloroacetamido-4-nitro-1-(2,6-dichloro-4-trifluoromethylsulphonyl-phenyl)-pyrazole of the formula

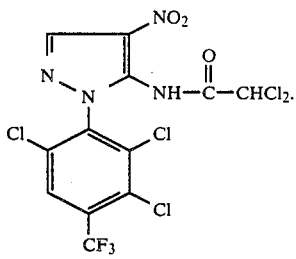

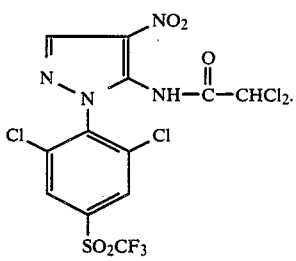

4. A compound according to claim 1, wherein such compound is 5-dichloroacetamido-(2,6-dichloro-3-fluoro-4-trifluoromethyl-phenyl)-4-nitropyrazole of the formula

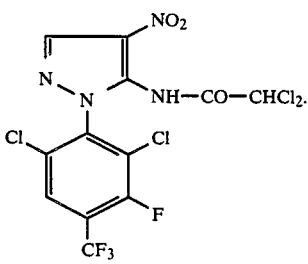

5. A compound according to claim 1, wherein such compound is 5-dichloroacetamido-4-nitro-1-(2-chloro-4-trifluoromethyl-phenyl)-pyrazole of the formula

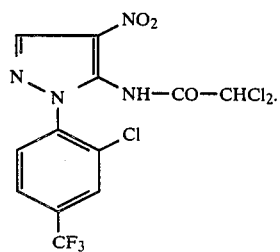

6. A compound according to claim 1, wherein such compound is 5-dichloroacetamido-4-nitro-1-(2-bromo-6-chloro-4-trifluoromethyl-phenyl)-pyrazole of the formula

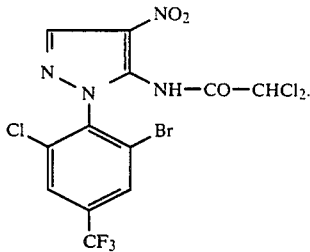

7. A compound according to claim 1, wherein such compound is 5-dichloroacetamido-4-nitro-1-(2-chloro-3-fluoro-4-trifluoromethyl-phenyl)-pyrazole of the formula

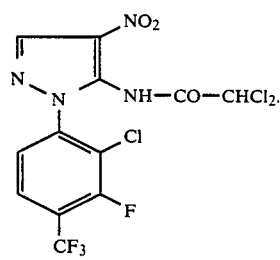

8. A herbicidal and plant growth-regulating composition comprising an amount effective therefor of a compound according to claim 1 and a diluent.

9. A method of combatting unwanted vegetation which comprises applying to such vegetation or to a locus from which such vegetation is to be excluded a herbicidally effective amount of a compound according to claim 1.

10. The method according to claim 9 wherein such compound is
5-dichloroacetamido-4-nitro-1-(2,3,6-trichloro-4-trifluoromethyl-phenyl)-pyrazole,
5-dichloroacetamido-4-nitro-1-(2,6-dichloro-4-trifluoromethylsulphonyl-phenyl)-pyrazole,
5-dichloroacetamido-(2,6-dichloro-3-fluoro-4-trifluoromethylphenyl)-4-nitropyrazole,
5-dichloroacetamido-4-nitro-1-(2-chloro-4-trifluoromethyl-phenyl)-pyrazole,
5-dichloroacetamido-4-nitro-1-(2-bromo-6-chloro-4-trifluoromethyl-phenyl)-pyrazole, or
5-dichloroacetamido-4-nitro-1-(2-chloro-3-fluoro-4-trifluoromethyl-phenyl)-pyrazole.

11. The method of regulating the growth of plants which comprises applying to such plants or to a locus in which such plants are growing or to be grown a plant growth-regulating effective amount of a compound according to claim 1.

12. The method according to claim 11 wherein such compound is
5-dichloroacetamido-4-nitro-1-(2,3,6-trichloro-4-trifluoromethyl-phenyl)-pyrazole,
5-dichloroacetamido-4-nitro-1-(2,6-dichloro-4-trifluoromethylsulphonyl-phenyl)-pyrazole,
5-dichloroacetamido-(2,6-dichloro-3-fluoro-4-trifluoromethyl-phenyl)-4-nitropyrazole,
5-dichloroacetamido-4-nitro-1-(2-chloro-4-trifluoromethyl-phenyl)-pyrazole,
5-dichloroacetamido-4-nitro-1-(2-bromo-6-chloro-4-trifluoromethyl-phenyl)-pyrazole, or
5-dichloroacetamido-4-nitro-1-(2-chloro-3-fluoro-4-trifluoromethyl-phenyl)-pyrazole.

* * * * *

UNITED STATES PATENT AND TRADEMARK OFFICE
CERTIFICATE OF CORRECTION

PATENT NO. : 4,764,202
DATED : August 16, 1988
INVENTOR(S) : Reinhold Gehring, et al It is certified that error appears in the above-identified patent and that said Letters Patent is hereby corrected as shown below:

| | |
|---|---|
| Col. 10, line 19 | Correct spelling of --Phleum-- |
| Col. 10, line 37 | Delete "trees" and substitute --tree-- |
| Col. 10, line 51 | Before "Experience" delete "p" |
| Col. 10, line 56 | Delete "state" and substitute --stage-- |
| Col. 11, line 31 | Delete "carries" and substitute --carriers-- |
| Col. 12, line 65 | Delete "compound" and substitute --compounds-- |
| Col. 19, line 21 | Top right of formula "(IV)" delete " $\diagup NO_2$ " |
| Col. 23, line 63 | After "fluoro-" delete "A" and substitute --4-- |

Signed and Sealed this

Fourteenth Day of February, 1989

Attest:

DONALD J. QUIGG

*Attesting Officer*     *Commissioner of Patents and Trademarks*